US009976703B2

(12) United States Patent
Hersak et al.

(10) Patent No.: US 9,976,703 B2
(45) Date of Patent: May 22, 2018

(54) REGULATOR APPARATUS HAVING A CHARGING VALVE ASSEMBLY AND A FLOW MULTIPLIER ASSEMBLY

(71) Applicant: ATOMIC ENERGY OF CANADA LIMITED/ÉNERGIE ATOMIQUE DU CANADA LIMITÉE, Chalk River (CA)

(72) Inventors: Greg Hersak, Deep River (CA); Richard Wilfrid Wray, Deep River (CA)

(73) Assignee: ATOMIC ENERGY OF CANADA LIMITED/ÉNERGY ATOMIQUE DU CANADA LIMITÉE, Chalk River (CA)

( * ) Notice: Subject to any disclaimer, the term of this patent is extended or adjusted under 35 U.S.C. 154(b) by 283 days.

(21) Appl. No.: 14/776,253

(22) PCT Filed: Mar. 14, 2014

(86) PCT No.: PCT/CA2014/050244
§ 371 (c)(1),
(2) Date: Sep. 14, 2015

(87) PCT Pub. No.: WO2014/138998
PCT Pub. Date: Sep. 18, 2014

(65) Prior Publication Data
US 2016/0033084 A1    Feb. 4, 2016

Related U.S. Application Data

(60) Provisional application No. 61/785,090, filed on Mar. 14, 2013.

(51) Int. Cl.
*F17C 13/04*  (2006.01)
*F15B 3/00*   (2006.01)
(Continued)

(52) U.S. Cl.
CPC ............... *F17C 13/04* (2013.01); *F15B 3/00* (2013.01); *F16K 1/36* (2013.01); *F16K 1/42* (2013.01);
(Continued)

(58) Field of Classification Search
USPC .............. 137/15.03, 505.13, 505.22, 505.25, 137/625.66; 60/325
See application file for complete search history.

(56) References Cited

U.S. PATENT DOCUMENTS 2,285,049 A * 6/1942 Parks ...................... E21B 43/12
                                                    137/505.13
2,504,720 A * 4/1950 Nixon .................... G05D 16/10
                                                    137/102
(Continued)

FOREIGN PATENT DOCUMENTS

CA        895122 A      3/1972
DE      1500511 A      4/1969
(Continued)

OTHER PUBLICATIONS

Extended European Search Report dated Oct. 20, 2016 in respect of European Application No. 14763231.9.
(Continued)

*Primary Examiner* — Jessica Cahill
*Assistant Examiner* — Daphne M Barry
(74) *Attorney, Agent, or Firm* — Bereskin & Parr LLP/S.E.N.C.R.L., s.r.l.

(57) ABSTRACT

A regulator apparatus for distributing a fluid may include a charging valve assembly and a flow multiplier assembly. In a recharge mode, a valve of the charging valve assembly is in an open position, and the fluid is received in a second cylinder of the flow multiplier assembly, causing first and second pistons of the flow multiplier assembly to move in a first direction. In a purge mode, the valve is in the seated position, and the fluid is received in a first cylinder of the flow multiplier assembly, causing the first and second pistons to move in a second direction, and discharging an outlet flow through an outlet of the flow multiplier assembly. The second cylinder may have a bore cross sectional area that is
(Continued)

greater than a bore cross sectional area of the first cylinder. Apparatuses disclosed herein may be implemented in a circumferential sampling tool.

22 Claims, 11 Drawing Sheets

(51) Int. Cl.
    *G21C 17/017*     (2006.01)
    *G01N 1/08*     (2006.01)
    *F16K 1/36*     (2006.01)
    *F16K 1/42*     (2006.01)
    *F16K 31/12*     (2006.01)
    *G21C 17/003*     (2006.01)
    *F15B 13/04*     (2006.01)

(52) U.S. Cl.
    CPC ............... *F16K 31/12* (2013.01); *G01N 1/08* (2013.01); *G21C 17/017* (2013.01); *F15B 13/0405* (2013.01); *G21C 17/003* (2013.01)

(56) References Cited

U.S. PATENT DOCUMENTS

| | | | |
|---|---|---|---|
| 2,568,262 A | | 9/1951 | Tucker |
| 2,592,940 A | | 4/1952 | Monoyer |
| 3,053,273 A | * | 9/1962 | Schreiner ............ A01C 23/024 137/505.13 |
| 3,948,051 A | | 4/1976 | Marshall |
| 4,628,881 A | | 12/1986 | Beck et al. |
| 4,845,982 A | | 7/1989 | Gilbert |
| RE33,270 E | | 7/1990 | Beck et al. |
| 6,170,508 B1 | | 1/2001 | Faust et al. |
| 6,532,943 B1 | | 3/2003 | Yudanov |
| 6,993,907 B2 | * | 2/2006 | Cooney ..................... B60T 8/26 60/563 |
| 7,398,765 B2 | | 7/2008 | Yamamoto |
| 7,461,795 B2 | | 12/2008 | Magel |
| 8,613,602 B2 | * | 12/2013 | Iversen ................. F04B 9/1056 417/225 |

FOREIGN PATENT DOCUMENTS

| | | |
|---|---|---|
| WO | 2007/115580 A1 | 10/2007 |
| WO | 2010/148479 A1 | 12/2010 |
| WO | 2011/038476 A1 | 4/2011 |
| WO | 2011/038478 A1 | 4/2011 |
| WO | 2011/104662 A1 | 9/2011 |

OTHER PUBLICATIONS

International Search Report dated May 30, 2014 in respect of International Application No. PCT/CA2014/050244.
International Preliminary Report on Patentability dated Sep. 15, 2014 in respect of International Application No. PCT/CA2014/050244.

\* cited by examiner

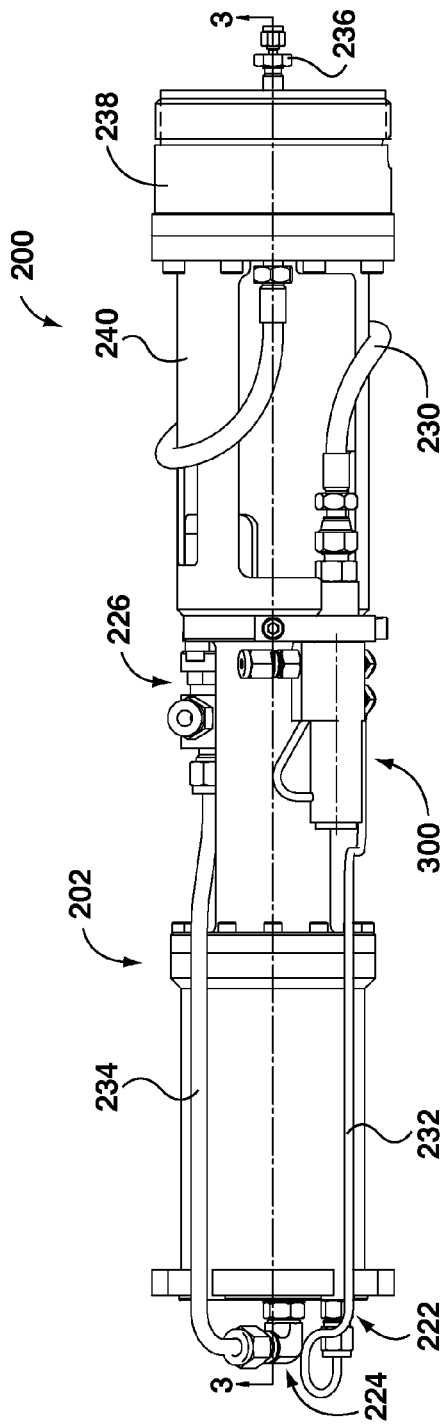
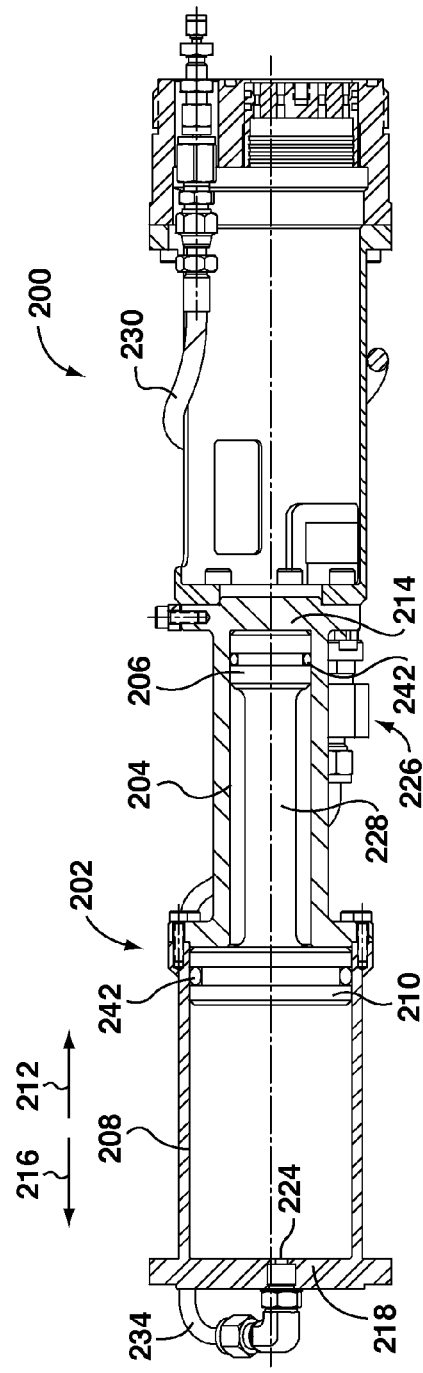
FIG. 2
FIG. 3

REGULATOR APPARATUS HAVING A CHARGING VALVE ASSEMBLY AND A FLOW MULTIPLIER ASSEMBLY

CROSS-REFERENCE TO RELATED APPLICATIONS

This is a national stage application of International Application No. PCT/CA2014/050244 filed on Mar. 14, 2014, which claims priority to U.S. Provisional Application No. 61/785,090 filed on Mar. 14, 2013, and the entire contents of each are hereby incorporated herein by reference.

FIELD

The present disclosure relates to apparatuses for providing fluid flows at different pressures. The present disclosure also relates to circumferential sampling tools having gripping mechanisms and a purge system.

BACKGROUND

International Application No. PCT/CA2009/001383 describes a circumferential sampling tool for obtaining samples from an interior wall of a tube. The tool has a cylindrical body, a shaft disposed in the cylindrical body, a first cutter, a second cutter being disposed at an angle to the first cutter, a third cutter, and a fourth cutter being disposed at an angle to the third cutter. The first, second, third and fourth cutters are operatively connected to the shaft for rotation therewith. Each of the cutters is movable radially between a retracted and an extended position in response to rotation of the shaft in order to obtain samples from the tube. A method of obtaining samples from an interior wall of a tube is also disclosed.

International Application No. PCT/CA2009/001385 describes a sampling tool for obtaining a sample from an interior wall of a tube. The tool includes first and second cutter sub-assemblies operatively connected to a shaft. First and second actuators move the first and second cutter sub-assemblies between a retracted position and an extended position as the shaft moves. A valve selectively fluidly communicates with an ejection port located in one of the first and second cutter sub-assemblies with a purge fluid supply. The valve discharges purge fluid through the ejection port onto the interior wall of the tube during cutting of a portion of the wall.

International Application No. PCT/CA2010/000781 describes a circumferential sampling tool for obtaining a sample from an interior wall of a tube. The tool has a cylindrical body with an aperture therein. First and second cutters are operatively connected to a shaft for rotation therewith. The first and second cutters are each movable radially between a retracted position and an extended position. First and second actuators are operatively connected to the first and second cutters respectively for moving the first and second cutters between their respective retracted and extended positions as the shaft rotates. Rotating the shaft causes the first cutter to move to the extended position thereby cutting a portion of the interior wall and then causes the second cutter to move to the extended position thereby cutting the sample from the interior wall from a location in the tube revealed by cutting the portion of the interior wall.

INTRODUCTION

The following is intended to introduce the reader to the detailed description that follows and not to define or limit the claimed subject matter.

In an aspect of the present disclosure, a regulator apparatus for distributing a fluid may include: a charging valve assembly including an inlet for receiving a feed flow of the fluid, a first charging outlet for discharging a recharge flow of the fluid, and a valve movable between an open position in which the inlet and the first charging outlet are connected in fluid communication, and a seated position in which flow between the inlet and the first charging outlet is blocked; and a flow multiplier assembly including a first cylinder having a first bore cross sectional area, a first piston arranged within the first cylinder, a second cylinder having a second bore cross sectional area that is greater than the first bore cross sectional area, and a second piston arranged within the second cylinder, the first and second pistons coupled together and movable in a first direction towards an endwall of the first cylinder and a second direction towards an endwall of the second cylinder, the first cylinder including a first port for receiving the feed flow of the fluid, the second cylinder including a second port connected in fluid communication to the first charging outlet for receiving the recharge flow of the fluid, and an outlet for discharging an outlet flow of the fluid. In a recharge mode, the valve is in the open position, and the fluid may be received in the second cylinder, causing the first and second pistons to move in the first direction. In a purge mode, the valve is in the seated position, and the fluid may be received in the first cylinder, causing the first and second pistons to move in the second direction, and discharging the outlet flow through the outlet.

In the purge mode, the outlet flow may be discharged by the second cylinder at a lower pressure and greater flow than the feed flow received by the first cylinder. The valve of the charging valve assembly may move between the open and seated positions based on a pressure of the feed flow of the fluid. The charging valve assembly may include a diversion conduit arranged so that the pressure of the feed flow of the fluid urges the valve to the seated position. The charging valve assembly may include a biasing member arranged to urge the valve to the open position. The valve may move from the open position to the seated position once the pressure of the feed flow of the fluid overcomes a force of the biasing member.

The apparatus may include a metering valve coupled to the outlet of the second cylinder. The charging valve assembly may include a supply port connected in fluid communication with the first port for supplying the feed flow of the fluid to the first cylinder. The first and second pistons may be connected by a shaft. The first port may be arranged in the endwall of the first cylinder or proximate thereto, and the second port may be arranged in the endwall of the second cylinder or proximate thereto. The outlet may be arranged in the endwall of the second cylinder or proximate thereto.

In an aspect of the present disclosure, a charging valve assembly may include: a body including an inlet, a first charging outlet, a supply channel connecting the inlet and the first charging outlet in fluid communication, and a valve cavity; a valve arranged in the valve cavity, and movable along a valve axis between an open position in which the inlet and the first charging outlet are connected in fluid communication, and a seated position in which flow between the inlet and the first charging outlet is blocked; and a diversion conduit connecting the supply channel to the valve cavity in fluid communication, and arranged so that pressure of a fluid in the supply channel urges the valve to the seated position.

The assembly may include a biasing member arranged to urge the valve to the open position. The valve may move from the open position to the seated position once the pressure of the fluid overcomes a force of the biasing member. The biasing member may be arranged within the valve cavity and generally surrounding the valve. The biasing member may include a spring.

The valve may extend lengthwise along the valve axis between a first end and a second end opposite the first end, and the diversion conduit may deliver the fluid to the valve cavity adjacent to second end of the valve. A cross sectional area of the valve cavity adjacent to the second end may be larger than a cross sectional area of the valve cavity adjacent to the first end.

The first end may seat against a seating surface when the valve is in the seated position. The first end may include a frustoconical surface, and the seating surface may be generally complementary in shape to the frustoconical surface. The seating surface may be arranged between the valve cavity and an end of the supply channel. The first charging outlet may be arranged within the valve cavity adjacent to the seating surface. The diversion conduit may be connected to the supply channel between the inlet and the seating surface. The assembly may include at least one second charging outlet connected to the supply channel between the inlet and the seating surface.

In an aspect of the present disclosure, a circumferential sampling tool may include the regulator apparatus as disclosed herein, and/or may include the charging valve assembly as disclosed herein.

In an aspect of the present disclosure, a method of distributing a fluid may include: providing a feed flow of the fluid to a charging valve assembly; supplying the feed flow of the fluid to a first cylinder of a flow multiplier assembly, the first cylinder having a first bore cross sectional area; in a recharge mode, supplying a recharge flow of the fluid from the charging valve assembly to a second cylinder of the flow multiplier assembly, the second cylinder having a second bore cross sectional area that is greater than the first bore cross sectional area; and in a purge mode, blocking the recharge flow of the fluid between the charging valve assembly and the second cylinder, and discharging an outlet flow of the fluid from the second cylinder. The outlet flow may be discharged by the second cylinder at a lower pressure than the feed flow received by the first cylinder.

In an aspect of the present disclosure, an apparatus may include: a charging valve assembly including an inlet for receiving a feed flow of the fluid, a first charging outlet for discharging a recharge flow of the fluid, and a valve movable between an open position in which the inlet and the first charging outlet are connected in fluid communication, and a seated position in which flow between the inlet and the first charging outlet is blocked; and a flow multiplier assembly including a first chamber having a first element movable to vary the volume of the first chamber, and a second chamber having a second element movable to vary the volume of the second chamber, the first and second elements being connected and arranged so that a movement of the first element and a corresponding movement of the second element gives a variation in the volume of the first chamber that is smaller than a variation in the volume of the second chamber, the first chamber including a first port for receiving the feed flow of the fluid, the second chamber including a second port connected in fluid communication to the first charging outlet for receiving the recharge flow of the fluid, and an outlet for discharging an outlet flow of the fluid. In a recharge mode, the valve is in the open position, and the fluid may be received in the second chamber, causing the first and second elements to move in a first direction. In a purge mode, the valve is in the seated position, and the fluid may be received in the first chamber, causing the first and second elements to move in a second direction, and discharging the outlet flow through the outlet.

Other aspects and features of the teachings disclosed herein will become apparent, to those ordinarily skilled in the art, upon review of the following description of the specific examples of the present disclosure.

BRIEF DESCRIPTION OF THE DRAWINGS

The drawings included herewith are for illustrating various examples of apparatuses and methods of the present disclosure and are not intended to limit the scope of what is taught in any way. In the drawings:

FIG. 2 is a top view of a regulator apparatus;
FIG. 3 is a sectional view along line 3-3 of FIG. 2.

DETAILED DESCRIPTION

Various apparatuses or methods will be described below to provide an example of an embodiment of each claimed invention. No embodiment described below limits any claimed invention and any claimed invention may cover apparatuses and methods that differ from those described below. The claimed inventions are not limited to apparatuses and methods having all of the features of any one apparatus or method described below, or to features common to multiple or all of the apparatuses or methods described below. It is possible that an apparatus or method described below is not an embodiment of any claimed invention. Any invention disclosed in an apparatus or method described below that is not claimed in this document may be the subject matter of another protective instrument, for example, a continuing patent application, and the applicant(s), inventor(s) and/or owner(s) do not intend to abandon, disclaim or dedicate to the public any such invention by its disclosure in this document.

One method of assessing the useful life of pressure tubes in nuclear reactors, such as a CANDU reactor, requires samples to be cut from the tube and analyzed for deuterium content. The deuterium concentration may then be used as a measure of the useful life of the remaining pressure tubes. However, this approach may be costly because of the shutdown period required to remove and replace a pressure tube. To avoid this shutdown period, a circumferential sampling tool may be used. Circumferential sampling tools are disclosed in International Application Nos. PCT/

CA2009/001383, PCT/CA2009/001385 and PCT/C2010/000781, and the entire contents of each are hereby incorporated herein by reference.

Figure 1:
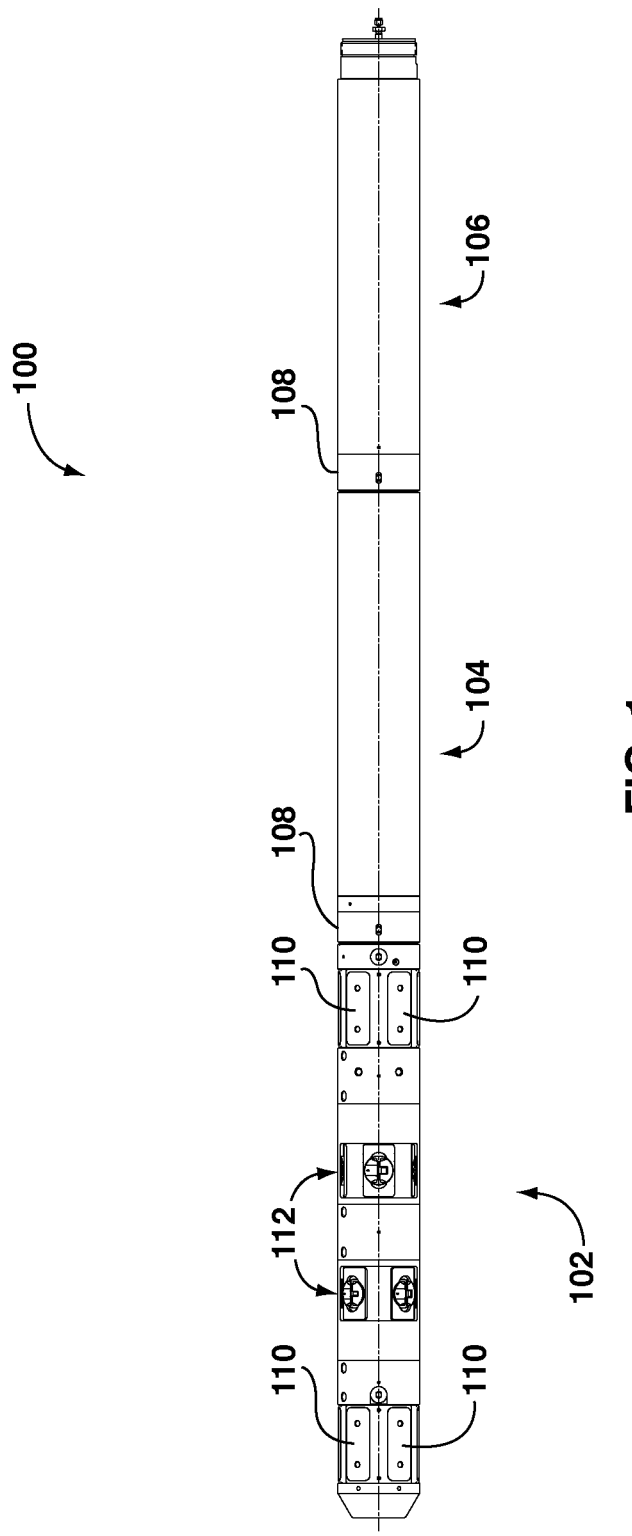
FIG. 1 is a side view of a circumferential sampling tool.
Figure 5:
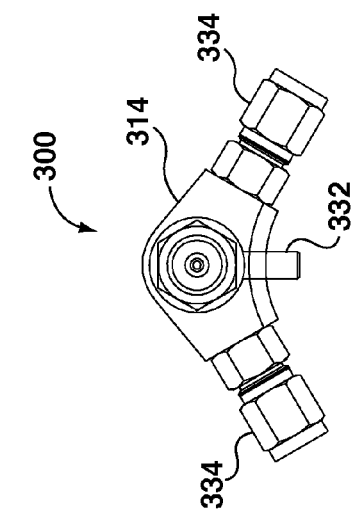
FIG. 5 is an end view of the charging valve assembly.
Figure 4:
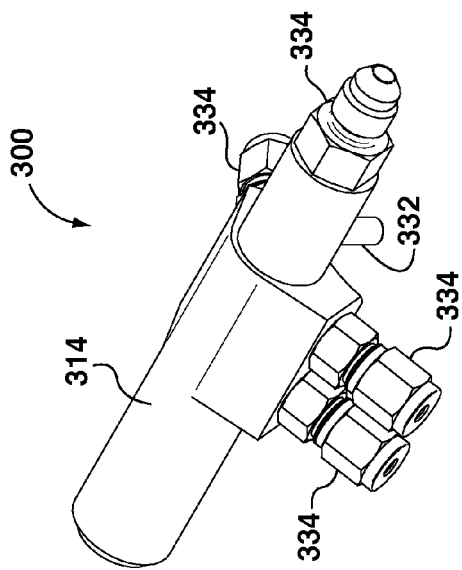
FIG. 4 is a perspective view of a charging valve assembly of the regulator apparatus.

Referring to FIG. 1, a circumferential sampling tool 100 is shown to include a carriage module 102, a drive module 104, and a hydraulic regulator module 106, which may be connected to each other by flexible joints 108. The carriage module 102 includes gripper or bearing pads 110 and cutter assemblies 112. Although not shown in FIG. 1, the cutter assemblies 112 may include a purge fluid system. The purge fluid system may be configured to discharge a purge fluid at cutting locations of the cutter assemblies 112. The purge fluid, which may be light water, may at least partially displace the heavy water at the cutting locations within the pressure tube, thereby protecting the fresh metal from contamination, and without having to drain the pressure tube.

The circumferential sampling tool 100 may require multiple hydraulic actuations to occur at different times and at different pressures and flow conditions. For example, the bearing pads 110 and the purge fluid system of the cutter assemblies 112 may require hydraulic fluid having different pressures and flow conditions. However, only a single hydraulic feed line may be available. This problem may be overcome by using pressure limiting valves and staging valves, an onboard hydraulic accumulator, and/or an onboard booster pump. These options may have drawbacks, such as requiring additional space or an active component that adds unnecessary and undesirable complexity to the tool. Additionally, with accumulators the outlet pressure may drop as the stored fluid volume is discharged, whereas it is desirable to have constant flow conditions, and pressure limiting valves may only work if sufficient inlet flow is available.

It is desirable to be able to provide multiple hydraulic actuations occurring at different times and at different pressures and flow conditions without the aforementioned drawbacks. It is also desirable to provide these multiple hydraulic actuations with a device that is compact, robust, straightforward and passive.

Referring to FIG. 2, an example of a regulator apparatus 200 is shown. The regulator apparatus 200 includes a charging valve assembly 300 and a flow multiplier assembly 202. The regulator apparatus 200 may be implemented in the hydraulic regulator module 106 of the circumferential sampling tool 100.

Referring to FIG. 3, the flow multiplier assembly 202 is shown to include a first cylinder 204 having a first bore cross sectional area, a first piston 206 arranged within the first cylinder 204, a second cylinder 208 having a second bore cross sectional area that is greater than the first bore cross sectional area, and a second piston 210 arranged within the second cylinder 208. The first and second pistons 206, 210 are shown coupled together and movable in a first direction 212 towards an endwall 214 of the first cylinder 204, and a second direction 216 towards an endwall 218 of the second cylinder 208. In the example illustrated, the first and second pistons 206, 210 are connected by a shaft 228.

Figure 7:
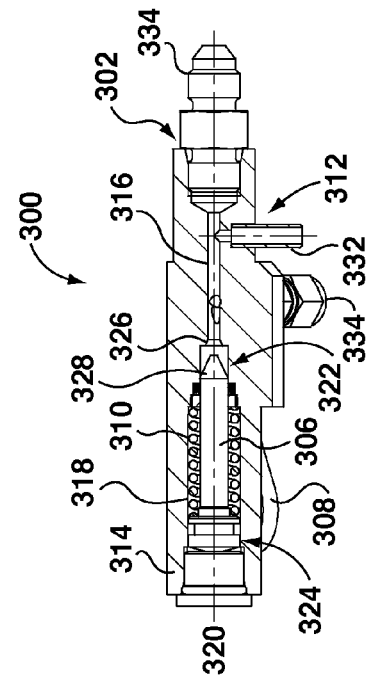
FIG. 7 is a sectional view along line 7-7 of FIG. 6.
Figure 6:
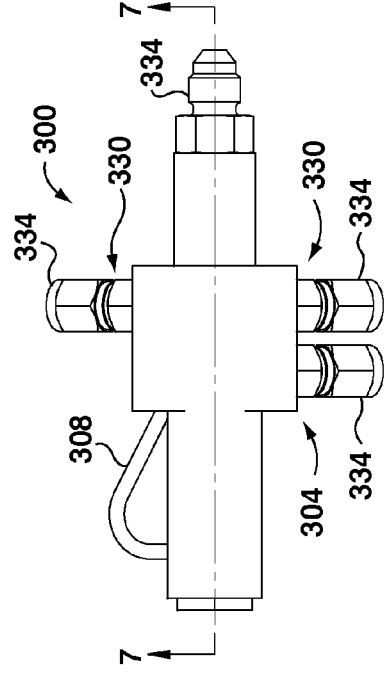
FIG. 6 is a top view of the charging valve assembly.
Figure 8:
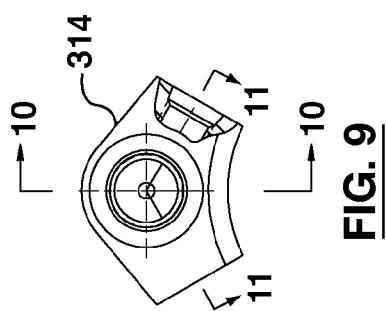
FIG. 8 is a perspective view of a body of the charging valve assembly.
Figure 9:
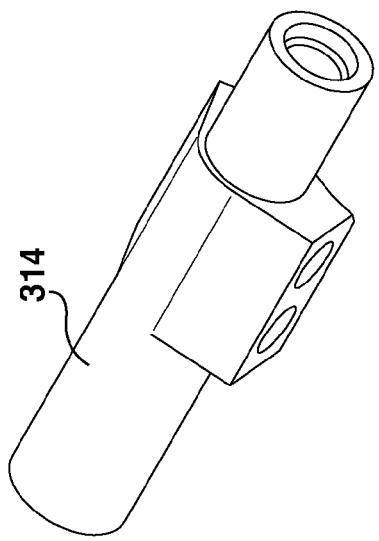
FIG. 9 is an end view of the body.
Figure 10:
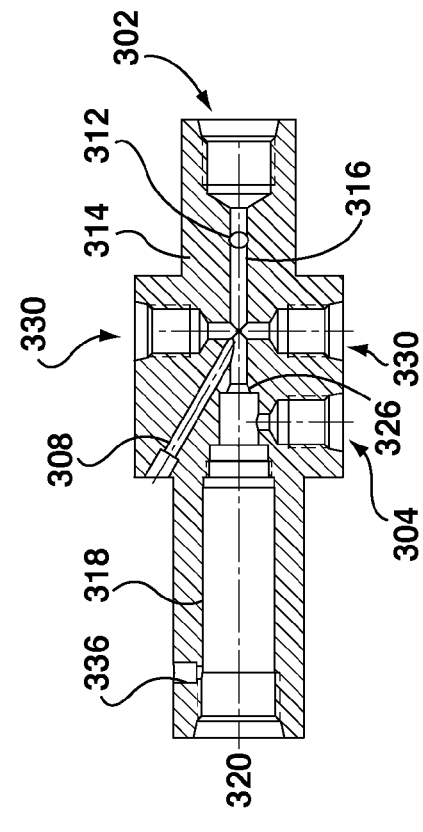
FIG. 10 is a sectional view along line 10-10 of FIG. 9.

Referring now to FIGS. 6 and 7, the charging valve assembly 300 includes an inlet 302 for receiving a feed flow of fluid, a first charging outlet 304 for discharging a recharge flow of the fluid, and a valve 306. The valve 306 is movable between an open position in which the inlet 302 and the first charging outlet 304 are connected in fluid communication, and a seated position in which flow between the inlet 302 and the first charging outlet 304 is blocked.

Figure 13:
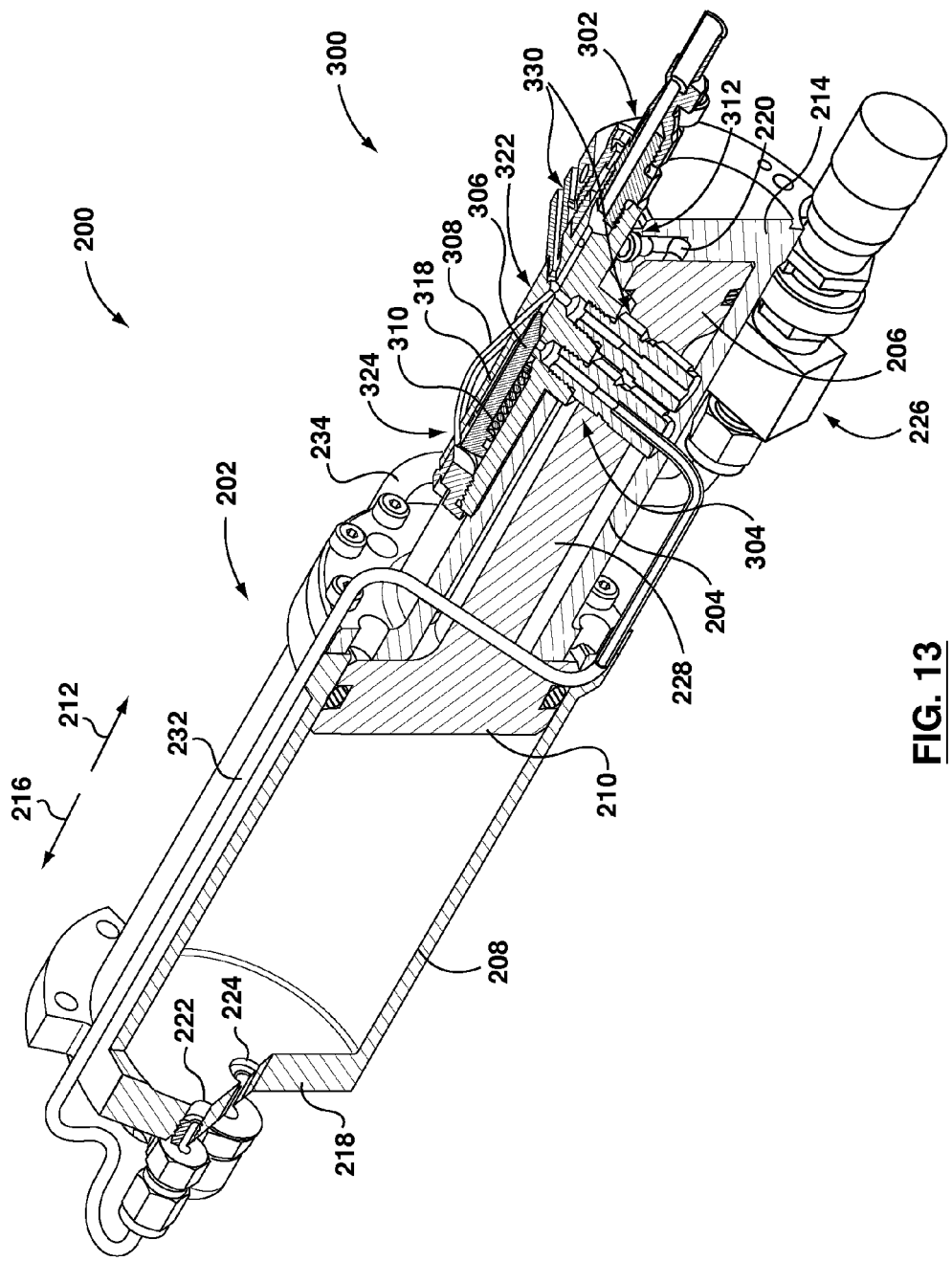
FIGS. 13 to 15 are cutaway sectional views of the regulator apparatus at the start, during, and the end of a purge mode, respectively.

Referring now to FIG. 13, the first cylinder 204 is shown to include a first port 220 for receiving the feed flow of the fluid from the charging valve assembly 300, and the second cylinder 208 includes a second port 222 for receiving the recharge flow of the fluid from the charging valve assembly 300. The second cylinder 208 further includes an outlet 224 for discharging an outlet flow of the fluid. In the example illustrated, the first port 220 is arranged in the endwall 214 of the first cylinder 204, and the second port 222 and the outlet 224 are arranged in the endwall 218 of the second cylinder 208. In other examples, the first port 220 may be arranged in the sidewall of the first cylinder 204 proximate to the endwall 214, and the second port 222 and the outlet 224 may be arranged in the sidewall of the second cylinder 208 proximate to the endwall 218.

When the regulator apparatus 200 is in a recharge mode, the valve 306 of the charging valve assembly 300 (FIG. 7) is in the open position, and the fluid is received in the second cylinder 208, causing the first and second pistons 206, 210 to move in the first direction 212. When the regulator apparatus 200 is in a purge mode, the valve 306 of the charging valve assembly 300 (FIG. 7) is in the seated position, and the fluid is received in the first cylinder 204, causing the first and second pistons 206, 210 to move in the second direction 216 and discharge the outlet flow through the outlet 224. In the purge mode, due to the difference in bore cross sectional areas of the cylinders 204, 208, the outlet flow is discharged by the second cylinder 208 at a lower pressure than the feed flow received by the first cylinder 204. In some examples, sizing of the cylinders 204, 208 may result in a roughly 4:1 flow increase/pressure decrease of the outlet flow versus the feed flow. In other examples, a ratio greater than 4:1, or less than 4:1, may be obtained by altering the diameters of the first cylinder 204 and the second cylinder 208.

Referring again to FIG. 3, the regulator apparatus 200 may further include an optional metering valve 226 for controlling the outlet flow, and is shown coupled to the outlet 224 of the second cylinder 208. In some examples, the metering valve 226 may be generally unaltered throughout cycles of recharge/modes. In other examples, the metering valve 226 may be configured to alternate between open and closed states. For example, the metering valve 226 may alternate between open and closed states, generally in synchronization with the purge and recharge modes, respectively, thereby preventing fluid flow through the outlet 224 during the recharge mode. In yet other examples, components downstream of the metering valve 226 may be configured to alternate between open and closed states, generally in synchronization with the purge and recharge modes, respectively, to prevent flow out of the outlet 224 during the recharge mode.

Referring again to FIGS. 6 and 7, the charging valve assembly 300 is shown to include a diversion conduit 308. The diversion conduit 308 is arranged so that the pressure of the feed flow of the fluid urges the valve 306 to the seated position. In the example illustrated, the charging valve assembly 300 includes a biasing member 310 that is arranged to urge the valve 306 to the open position. The valve 306 may move from the open position to the seated position once the pressure of the feed flow of the fluid overcomes a force of the biasing member 310. The charging valve assembly 300 further includes a supply port 312 that is connected in fluid communication with the first port 220 of the flow multiplier assembly 202 for supplying the feed flow of the fluid to the first cylinder 204.

Referring now to FIGS. 4 to 11, the charging valve assembly 300 includes a body 314. The body 314 includes the inlet 302, the first charging outlet 304, a supply channel 316 that connects the inlet 302 and the first charging outlet 304 in fluid communication, and a valve cavity 318. In the example illustrated, the valve 306 is arranged in the valve cavity 318 and moves along a valve axis 320 between the open and seated positions. The diversion conduit 308 connects the supply channel 316 to the valve cavity 318 in fluid communication. The body 314 is shown to include an aperture 336 connecting the diversion conduit 308 to the valve cavity 318. The diversion conduit 308 is arranged so that the pressure of the feed flow of the fluid in the supply channel 316 via the diversion conduit 308 urges the valve 306 to the seated position. The biasing member 310 is shown as a spring that is arranged within the valve cavity 318, and generally surrounds the valve 306.

Referring in particular to FIG. 7, the valve 306 extends lengthwise along the valve axis 320 between a first end 322 and a second end 324 opposite the first end 322. The diversion conduit 308 delivers the fluid to the valve cavity 318 adjacent to the second end 324 of the valve 306. In the example illustrated, a cross sectional area of the valve cavity 318 adjacent to the second end 324 is larger than a cross sectional area of the valve cavity 318 adjacent to the first end 322, in order to bias the valve 306 to the seated position. The first end 322 seats against a seating surface 326 when the valve 306 is in the seated position. The seating surface 326 is shown arranged between the valve cavity 318 and an end of the supply channel 316. In the example illustrated, the first end 322 includes a frustoconical surface 328, and the seating surface 326 may be generally complementary in shape to the frustoconical surface 328 to ensure a fluid tight fit.

Figure 11:
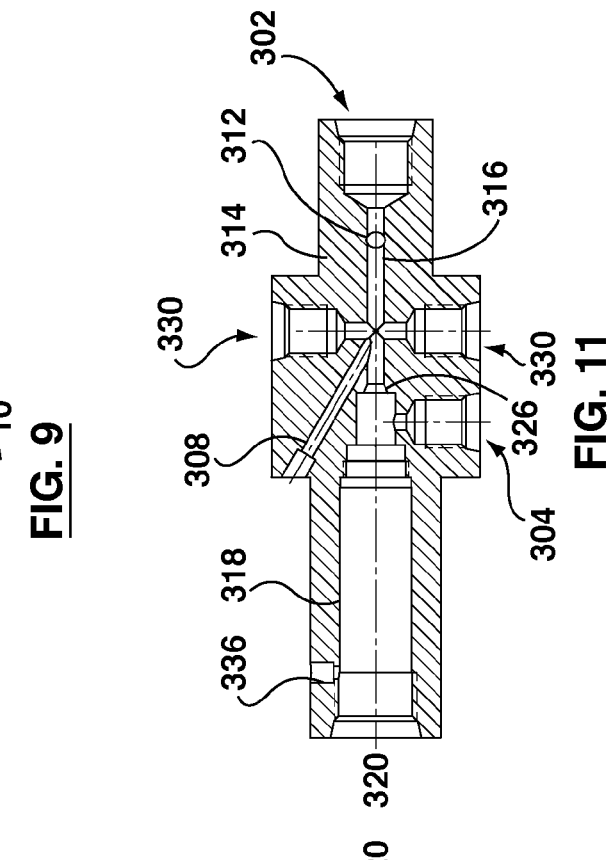
FIG. 11 is a sectional view along line 11-11 of FIG. 9.

Referring in particular to FIG. 11, the first charging outlet 304 is shown arranged within the valve cavity 318 adjacent to the seating surface 326, and the diversion conduit 308 is connected to the supply channel 316 between the inlet 302 and the seating surface 326. In the example illustrated, the charging valve assembly 300 further includes two second charging outlets 330, which are connected to the supply channel 316 between the inlet 302 and the seating surface 326, upstream of the first charging outlet 304.

Referring again to FIGS. 2 and 3, the regulator apparatus 200 is shown to include a feed line 230 that provides a feed flow of fluid to the charging valve assembly 300, a recharge line 232 that connects the second port 222 of the second cylinder 208 to the first charging outlet 304 of the charging valve assembly 300, an outlet line 234 that connects the outlet 224 to the metering valve 226, a coupling 236 that connects the feed line 230 to a feed fluid supply (not shown), a housing 238, and an inner shell 240. The first and second pistons 206, 210 are shown to each include O-rings 242.

Referring again to FIGS. 4 to 7, the supply port 312 of the charging valve assembly 300 is shown to connect to a supply line 332 for delivering the feed flow (to the first port 220), and the charging valve assembly 300 further includes connectors 334 at the inlet 302, first charging outlet 304, and the second charging outlets 330.

Figure 12:
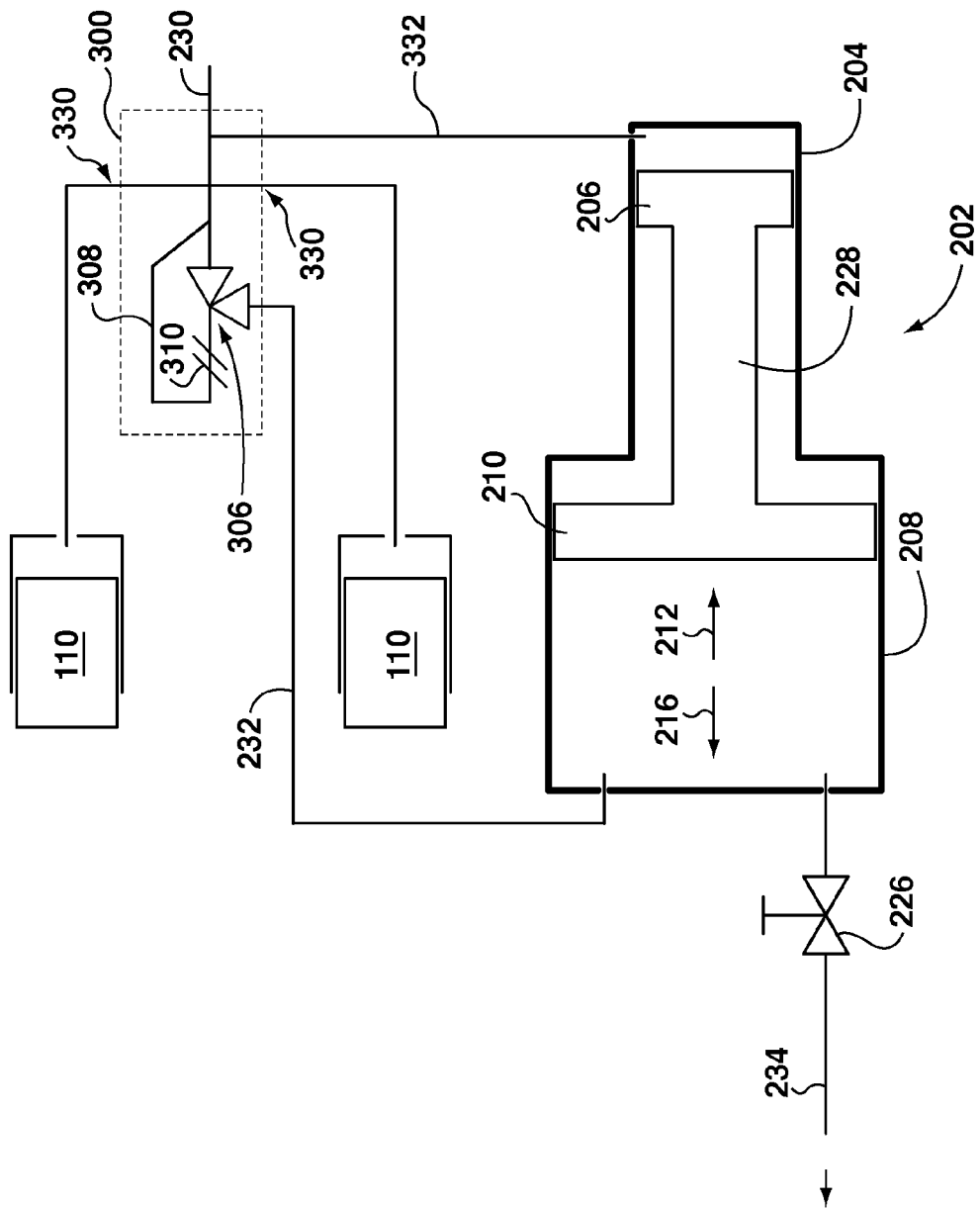
FIG. 12 is a schematic diagram of a hydraulic system of the circumferential sampling tool of FIG. 1, and including the regulator apparatus.

FIG. 12 shows an exemplary configuration of the charging valve assembly 300 and the flow multiplier assembly 202 implemented in a hydraulic system for the circumferential sampling tool 100 (FIG. 1). In FIG. 12, feed flow of the fluid is supplied to the system through the feed line 230 from a feed fluid supply. The feed fluid is directed by the charging valve assembly 300 through the second charging outlets 330 to actuate the bearing pads 110. Feed fluid is also directed by the charging valve assembly 300 to the cylinders 204, 208 through the lines 332, 232, respectively. When feed fluid is directed to the first cylinder 204 (in the purge mode), the first piston 206, the second piston 210, and the shaft 228 move in the second direction 216. When feed fluid is directed to the second cylinder 208 (in the recharge mode), the first piston 206, the second piston 210, and the shaft 228 move in the first direction 212.

In the example illustrated, the valve 306 controls whether feed fluid is directed to the second cylinder 208 or not. The biasing member 310 and the diversion conduit 308 dictate whether the valve 306 is in the open position or the seated position, and the valve 306 of the charging valve assembly 300 may move between the open and seated positions based on a pressure of the feed flow of the fluid, as described in greater detail below. When the second piston 210 moves in the second direction 216, fluid exits the flow multiplier assembly 202 through the metering valve 226 and the outlet line 234, and this fluid may be used to supply the purge fluid system for the cutter assemblies 112 of the circumferential sampling tool 100 (FIG. 1).

With reference to FIGS. 13 to 18, operation of the regulator apparatus 200 and the charging valve assembly 300 between the purge and recharge modes will be described in greater detail.

Referring to FIG. 13, at the start of the purge mode, the inlet 302 of the charging valve assembly 300 may supplied with a fluid flow at a relatively high pressure (e.g., 3000 psi). At this high pressure, fluid acting through the diversion conduit 308 exerts a seating force on the second end 324 of the valve 306 sufficient to overcome an opening force on the valve 306 exerted by the biasing member 310 and the fluid acting on the first end 322 of the valve 306. The seating force may be greater than the opening force as a consequence of the larger cross sectional area of the valve cavity 318 adjacent to the second end 324 than the cross section area of the valve cavity 318 adjacent to the first end 322. The greater seating force causes the valve 306 to move to the seated position, as shown in FIG. 13, blocking fluid communication between the inlet 302 and the first charging outlet 304. When the valve 306 is in the seated position, the fluid within the second cylinder 208 may be isolated from the high pressure of the inlet 302 and may remain at a low pressure.

The high pressure fluid flow via the inlet 302 of the charging valve assembly 300 acts on the first piston 206 through the supply port 312 and first port 220 of the first cylinder 204, which generates a purging force on the first piston 206. The purging force is in the second direction 216. When the second piston 210 moves in the second direction 216, the outlet fluid exits the second cylinder 208 through the outlet 224 at low pressure. The outlet fluid from the second cylinder 208 is at a higher flow rate than feed fluid received by the first cylinder 204. As mentioned above, in some examples, sizing of the cylinders 204, 208 may result in a roughly 4:1 flow increase/pressure decrease of the outlet flow versus the feed flow (and therefore the pressure at the outlet port 224 may be, e.g., 750 psi). In other examples, a ratio greater than 4:1, or less than 4:1, may be obtained by altering the diameters of the first cylinder 204 and the second cylinder 208.

Figure 14:
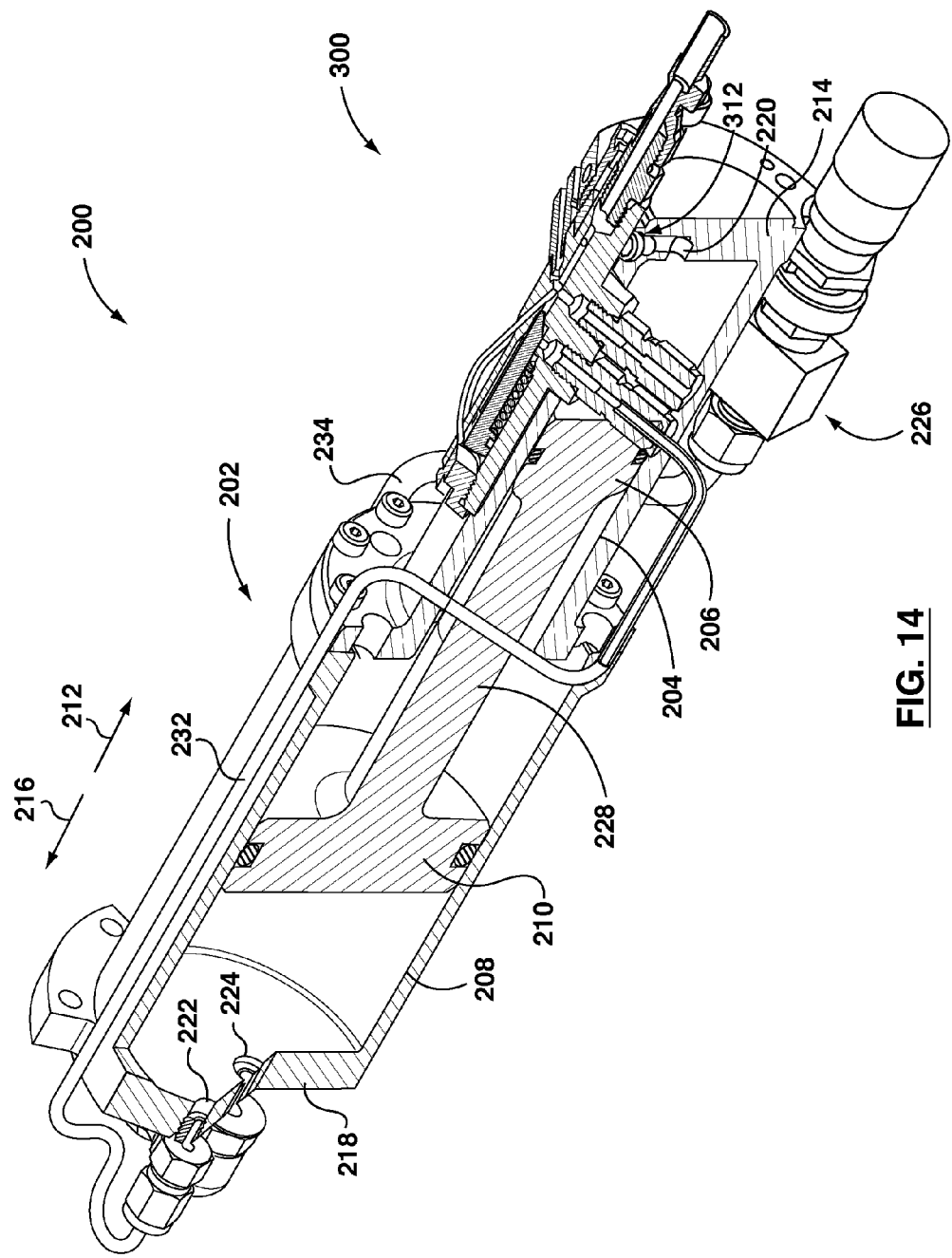

Referring to FIG. 14, during the purge mode, the first piston 206, second piston 210 and shaft 228 continue to move in the second direction 216, and the outlet fluid continues to exit the second cylinder 208 through the outlet 224.

Figure 15:
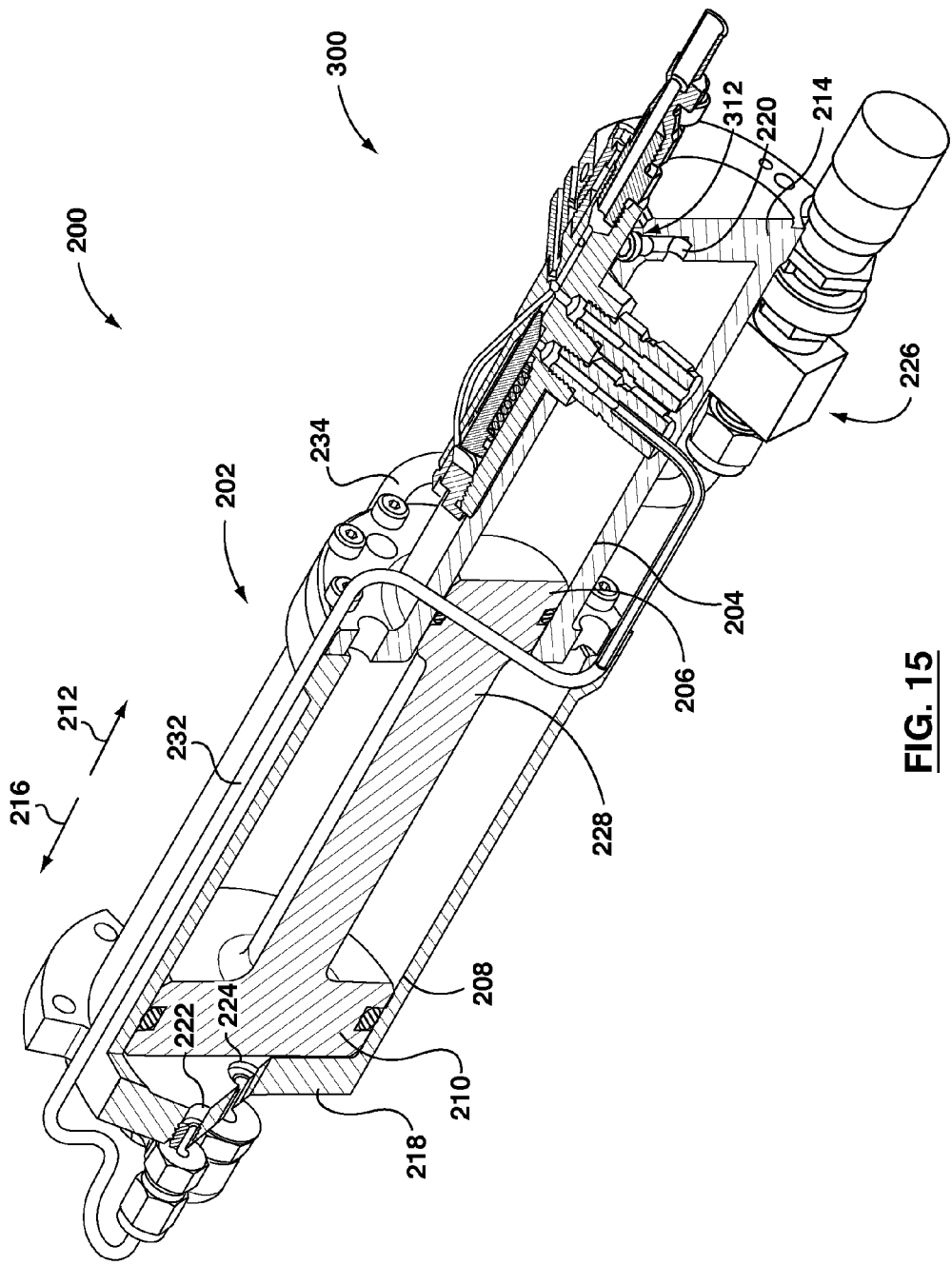

Referring to FIG. 15, at the end of the purge mode, the second piston 210 is shown abutting the endwall 218 of the second cylinder 208, and the first piston 206, second piston 210 and shaft 228 are no longer moving in the second direction 216.

Figure 16:
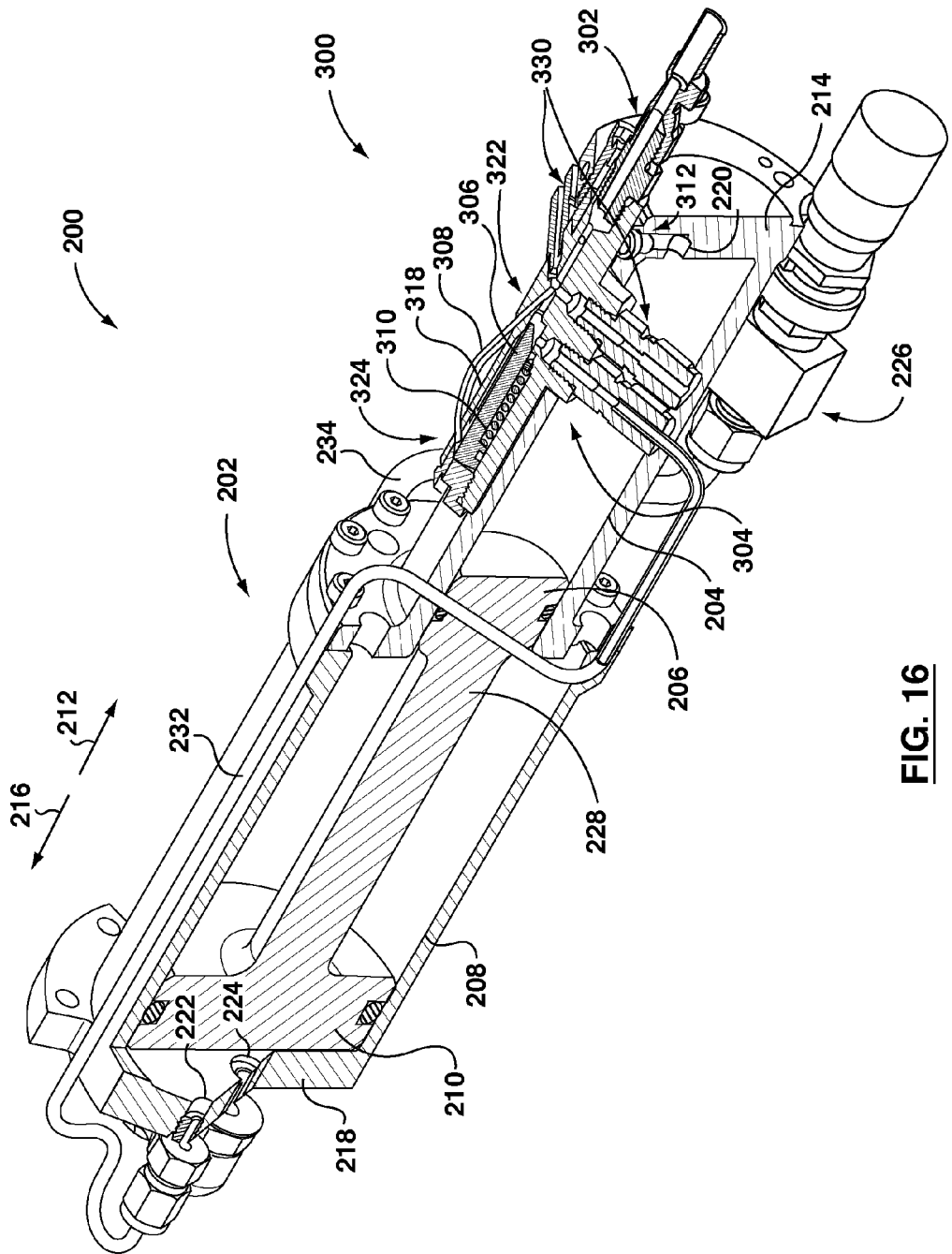
FIGS. 16 to 18 are cutaway sectional views of the regulator apparatus at the start, during, and the end of a recharge mode, respectively.

Referring to FIG. 16, at the start of the recharge mode, the inlet 302 of the charging valve assembly 300 is now supplied with a fluid flow at a relatively low pressure (e.g., 300 psi). At this low pressure, the seating force on the second end 324 of the valve 306 is insufficient to overcome the opening force, and the valve 306 moves to the open position, as shown in FIG. 16. When the valve 306 is in the open position, the inlet 302 is in fluid communication with the first charging outlet 304, and the low pressure fluid flow is received in the second cylinder 208 through the second port 222. The first cylinder 204 may still be in fluid communication with the inlet 302 through the first port 220 and the supply port 312, and may be at the low pressure.

The low pressure fluid flow acts on the first piston 206 through the supply port 312 and the first port 220 of the first cylinder 204, which generates the purging force on the first piston 206. The purging force is in the second direction 216. The low pressure fluid flow within the second cylinder 208 generates a recharging force on the second piston 210. The recharging force is in the first direction 212. Since the second bore cross sectional area of the second cylinder 208 is larger than the first bore cross sectional area of the first cylinder 204, the recharging force is larger than the purging force, and causes the first piston 206, second piston 210 and shaft 228 to move in the first direction 212.

When the first piston 206 and second piston 210 move in the first direction 212, low pressure fluid exit the first cylinder 204 through the first port 220 and low pressure fluid is received in the second cylinder 208 through the second port 222.

Figure 17:
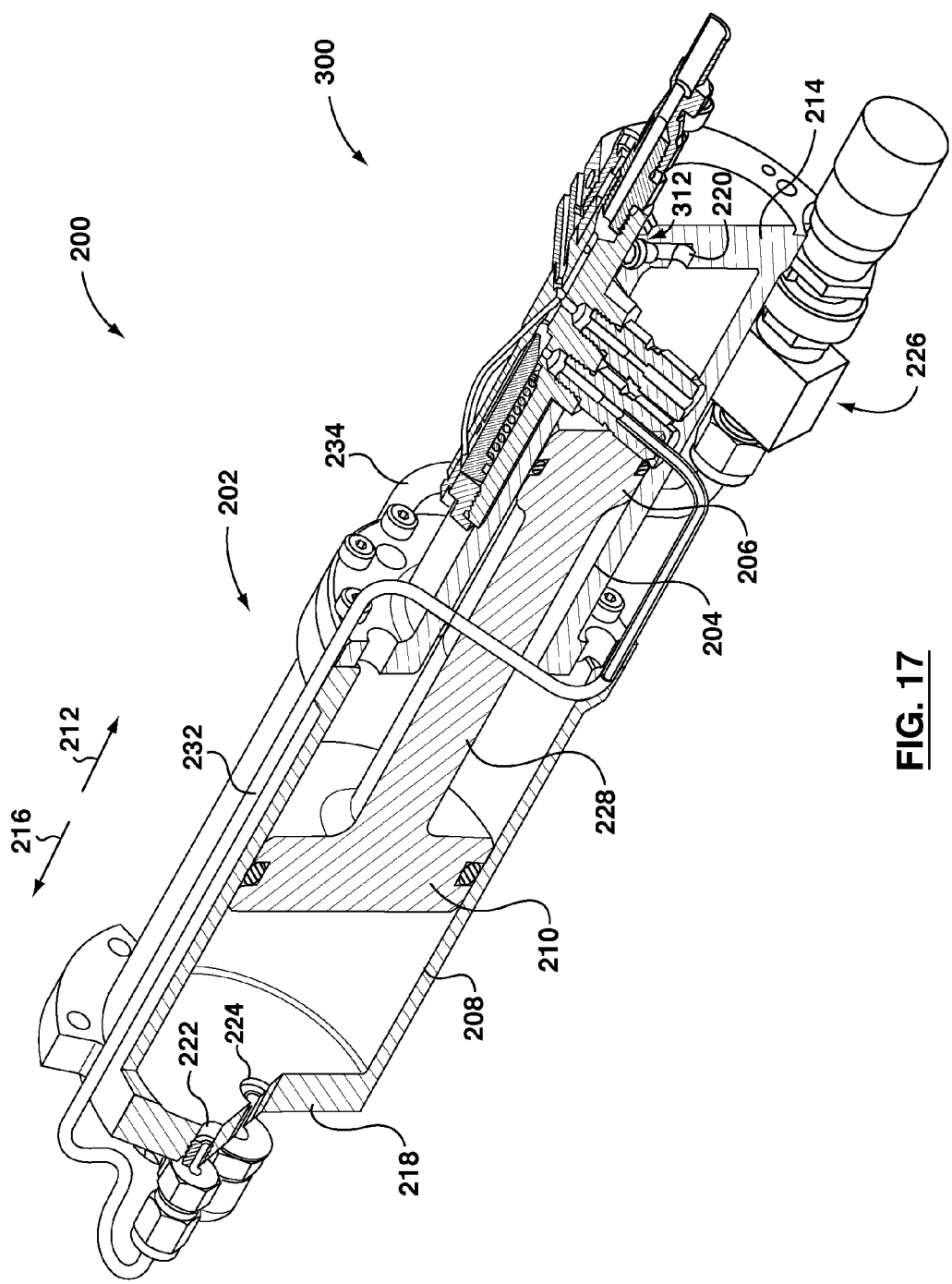

Referring to FIG. 17, during the recharge mode, the first piston 206, the second piston 210 and the shaft 228 may continue to move in the first direction 212. Low pressure fluid continues to be received in the second cylinder 208 through the second port 222, and continues to exit the first cylinder 204 through the first port 220.

Figure 18:
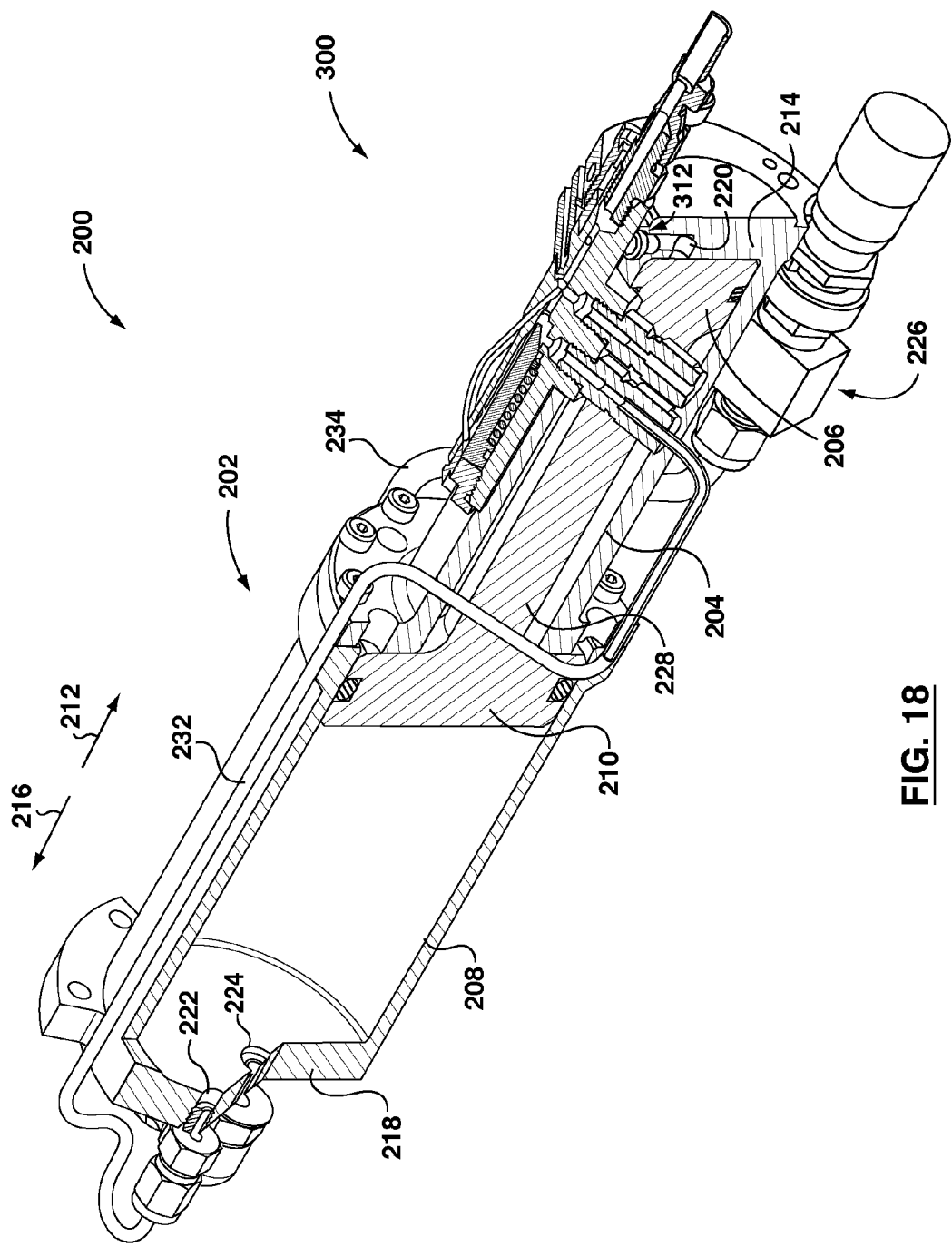

Referring to FIG. 18, at the end of the recharge mode, the first piston 206 is shown abutting the endwall 214 of the first cylinder 204, and the first piston 206, second piston 210 and shaft 228 are no longer moving in the first direction 212. The inlet 302 of the charging valve assembly 300 may again be supplied with a fluid flow at a relatively high pressure to initiate another purge mode. In this manner, cycles of purging and recharging may be controlled solely by means of controlling cycles of high/low pressure of the fluid being supplied to the charging valve assembly 300.

Although the apparatuses and methods of the present disclosure are described in the context of a circumferential sampling tool, which may be used for sampling pressure tubes in nuclear reactors, the apparatuses and methods described herein may be used in other operations requiring multiple hydraulic actuations to occur at different times and at different pressure and flow conditions.

While the above description provides examples of one or more methods or apparatuses, it will be appreciated that other methods or apparatuses may be within the scope of the accompanying claims.

We claim:

1. A regulator apparatus for distributing a fluid, the apparatus comprising:
   a charging valve assembly comprising an inlet for receiving a feed flow of the fluid, a first charging outlet for discharging a recharge flow of the fluid, and a valve movable between an open position in which the inlet and the first charging outlet are connected in fluid communication, and a seated position in which flow between the inlet and the first charging outlet is blocked; and
   a flow multiplier assembly comprising a first cylinder, a first piston arranged within the first cylinder, a second cylinder, and a second piston arranged within the second cylinder, the first and second pistons coupled together and movable in a first direction towards an endwall of the first cylinder and a second direction towards an endwall of the second cylinder, the first cylinder having a first bore cross sectional area perpendicular to the first direction, the second cylinder having a second bore cross sectional area perpendicular to the second direction, the second bore cross sectional area being greater than the first bore cross sectional area, the first cylinder comprising a first port for receiving the feed flow of the fluid, the second cylinder comprising a second port connected in fluid communication to the first charging outlet for receiving the recharge flow of the fluid, and an outlet for discharging an outlet flow of the fluid,
   wherein, in a recharge mode, the valve is in the open position, and the recharge flow of the fluid is received in the second cylinder, causing the first and second pistons to move in the first direction, and
   wherein, in a purge mode, the valve is in the seated position, and the feed flow of the fluid is received in the first cylinder, causing the first and second pistons to move in the second direction, and discharging the outlet flow through the outlet.

2. The apparatus of claim 1, wherein, in the purge mode, the outlet flow is discharged by the second cylinder at a lower pressure and greater flow than the feed flow received by the first cylinder.

3. The apparatus of claim 1, wherein the valve of the charging valve assembly moves between the open and seated positions based on a pressure of the feed flow of the fluid.

4. The apparatus of claim 3, wherein the charging valve assembly comprises a diversion conduit arranged so that the pressure of the feed flow of the fluid urges the valve to the seated position.

5. The assembly of claim 4, wherein the charging valve assembly comprises a biasing member arranged to urge the valve to the open position.

6. The assembly of claim 5, wherein the valve moves from the open position to the seated position once the pressure of the feed flow of the fluid overcomes a force of the biasing member.

7. The apparatus of claim 1, comprising a metering valve coupled to the outlet of the second cylinder.

8. The apparatus of claim 1, wherein the charging valve assembly comprises a supply port connected in fluid communication with the first port for supplying the feed flow of the fluid to the first cylinder.

9. The apparatus of claim 1, wherein the first and second pistons are connected by a shaft.

10. The apparatus of claim 1, wherein the first port is arranged in the endwall of the first cylinder or proximate thereto, and the second port is arranged in the endwall of the second cylinder or proximate thereto.

11. The apparatus of claim 1, wherein the outlet is arranged in the endwall of the second cylinder or proximate thereto.

12. A charging valve assembly, comprising:
a body comprising an inlet, a first charging outlet, a supply channel connecting the inlet and the first charging outlet in fluid communication, and a valve cavity;
a valve arranged in the valve cavity, and movable along a valve axis between an open position in which the inlet and the first charging outlet are connected in fluid communication, and a seated position in which flow between the inlet and the first charging outlet is blocked; and
a diversion conduit connecting the supply channel to the valve cavity in fluid communication, and arranged so that pressure of a fluid in the supply channel urges the valve to the seated position,
wherein the valve extends lengthwise along the valve axis between a first end and a second end opposite the first end, and the diversion conduit delivers the fluid to the valve cavity adjacent to second end of the valve,
wherein a cross sectional area of the valve cavity perpendicular to the valve axis adjacent to the second end is larger than a cross sectional area of the valve cavity perpendicular to the valve axis adjacent to the first end,
wherein the first end seats against a seating surface when the valve is in the seated position, and
comprising at least one second charging outlet connected to the supply channel between the inlet and the seating surface.

13. The assembly of claim 12, comprising a biasing member arranged to urge the valve to the open position.

14. The assembly of claim 13, wherein the valve moves from the open position to the seated position once the pressure of the fluid overcomes a force of the biasing member.

15. The assembly of claim 13, wherein the biasing member is arranged within the valve cavity and the biasing member at least partially surrounds the valve.

16. The assembly of claim 15, wherein the biasing member comprises a spring.

17. The assembly of claim 12, wherein the first end comprises a frustoconical surface, and the seating surface is shaped for a fluid tight fit with the frustoconical surface.

18. The assembly of claim 12, wherein the seating surface is arranged between the valve cavity and an end of the supply channel.

19. The assembly of claim 12, wherein the first charging outlet is arranged within the valve cavity adjacent to the seating surface.

20. The assembly of claim 12, wherein the diversion conduit is connected to the supply channel between the inlet and the seating surface.

21. A method of distributing a fluid, the method comprising:
providing a feed flow of the fluid to a charging valve assembly;
supplying the feed flow of the fluid to a first cylinder of a flow multiplier assembly, the first cylinder having a first bore cross sectional area perpendicular to a first direction in which a first piston moves within the first cylinder;
in a recharge mode, supplying a recharge flow of the fluid from the charging valve assembly to a second cylinder of the flow multiplier assembly, the second cylinder having a second bore cross sectional area perpendicular to a second direction in which a second piston moves within the second cylinder, the second bore cross sectional area being greater than the first bore cross sectional area; and
in a purge mode, blocking the recharge flow of the fluid between the charging valve assembly and the second cylinder, and discharging an outlet flow of the fluid from the second cylinder,
wherein the outlet flow is discharged by the second cylinder at a lower pressure than the feed flow received by the first cylinder.

22. An apparatus comprising:
a charging valve assembly comprising an inlet for receiving a feed flow of the fluid, a first charging outlet for discharging a recharge flow of the fluid, and a valve movable between an open position in which the inlet and the first charging outlet are connected in fluid communication, and a seated position in which flow between the inlet and the first charging outlet is blocked; and
a flow multiplier assembly comprising a first chamber having a first element movable to vary the volume of the first chamber, and a second chamber having a second element movable to vary the volume of the second chamber, the first and second elements being connected and arranged so that a movement of the first element and a corresponding movement of the second element gives a variation in the volume of the first chamber that is smaller than a variation in the volume of the second chamber, the first chamber comprising a first port for receiving the feed flow of the fluid, the second chamber comprising a second port connected in fluid communication to the first charging outlet for receiving the recharge flow of the fluid, and an outlet for discharging an outlet flow of the fluid,
wherein, in a recharge mode, the valve is in the open position, and the fluid is received in the second chamber, causing the first and second elements to move in a first direction, and
wherein, in a purge mode, the valve is in the seated position, and the fluid is received in the first chamber, causing the first and second elements to move in a second direction, and discharging the outlet flow through the outlet.

* * * * *